United States Patent [19]

Tanaka

[11] Patent Number: 6,149,598
[45] Date of Patent: Nov. 21, 2000

[54] ULTRASOUND ENDOSCOPE

[75] Inventor: Toshizumi Tanaka, Omiya, Japan

[73] Assignee: Fuji Photo Optical Co., Ltd., Omiya, Japan

[21] Appl. No.: 09/277,768

[22] Filed: Mar. 29, 1999

[30] Foreign Application Priority Data

Mar. 31, 1998 [JP] Japan .................................. 10-101846

[51] Int. Cl.⁷ ...................................................... A61B 8/00
[52] U.S. Cl. ............................................ 600/462; 600/437
[58] Field of Search .................................. 600/437, 462,
600/461, 439, 435, 440

[56] References Cited

U.S. PATENT DOCUMENTS

| 4,135,406 | 1/1979 | Kretz . | |
| 4,763,662 | 8/1988 | Yokoi | ...................... 600/461 |
| 5,398,690 | 3/1995 | Batten et al. | ........................... 600/439 |
| 5,471,988 | 12/1995 | Fujio et al. | ........................... 600/439 |
| 5,485,842 | 1/1996 | Quistgaard . | |

FOREIGN PATENT DOCUMENTS

| 358 155 | 1/1980 | Austria . |
| 001 708 | 9/1997 | Austria . |
| 0 754 957 | 1/1997 | European Pat. Off. . |
| 0 806 682 | 11/1997 | European Pat. Off. . |
| 0 813 074 | 12/1997 | European Pat. Off. . |
| WO 96/00402 | 1/1996 | WIPO . |

*Primary Examiner*—Marvin M. Lateef
*Assistant Examiner*—Maulin Patel
*Attorney, Agent, or Firm*—Oblon, Spivak, McClelland, Maier & Neustadt, P.C.

[57] ABSTRACT

An ultrasound endoscope having an endoscopic observation system along with an ultrasound scan system. An outlet opening of an instrument passage, which is shunted from a biopsy channel of the endoscope, is located within a view field of an endoscopic image pickup window, which largely overlaps a scan range of the ultrasound scan system. A puncture instrument having a sharp-pointed rigid needle at the instrument outlet opening, which is in the view field of the endoscopic image pickup, can be monitored by way of the endoscopic observation system to check its position for safety purposes, from a slightly projected position to a largely projected position whenever it spontaneously gets out of the instrument outlet opening. Once the puncture needle is driven into an intracavitary wall toward a diseased portion in target, it can be monitored through the ultrasound scan system.

4 Claims, 6 Drawing Sheets

ULTRASOUND ENDOSCOPE

BACKGROUND OF THE INVENTION

1. Field of the Art

This invention relates generally to an ultrasound endoscope to be introduced into a body cavity of a patient for making ultrasound scans of internal body tissues in addition to an endoscopic examination, and more particularly to an ultrasound endoscope which is so arranged as to guarantee safe use of a puncture instrument or similar treating instruments.

2. Prior Art

Endoscopes and ultrasound probes are in wide use especially in medical fields for examining intracavitary portions for diagnostic or therapeutical purposes. An endoscopes is used mainly for examination of surface conditions of intracavitary walls, while an ultrasound probe is used for scanning internal body tissues. Besides, there have also been in wide use the so-called ultrasound endoscopes which are equipped with an ultrasound scanning system along with an endoscopic observation system. More particularly, ultrasound endoscopes are generally provided with an endoscopic or optical observation system, including an illuminating or lighting system and an image pickup system which are incorporated into a distal end portion of an elongated flexible insertion instrument, and an ultrasound scan system including an ultrasound transducer which is also incorporated into the distal end portion of the insertion instrument. It is usually the case that the distal end of the flexible insertion instrument is constituted by a rigid casing structure, and accommodates an endoscopic observation system and an ultrasound scan system side by side in the radial direction. In this regard, in most cases, an ultrasound scanner including an ultrasound transducer is located forward of an endoscopic image pickup portion of the endoscopic observation system. In addition, in order to introduce the endoscopic insertion instrument into a body cavity in compliance with the shape of a duct or a path of insertion which may contain bends on the way as in the case of peroral insertion, an angle section or a flexible joint is attached to the rigid distal end casing structure which constitutes a rigid distal end section of the endoscopic insertion instrument.

When a diseased portion is detected in internal body tissues as a result of an examination by an ultrasound endoscope as described above, it is desirable for the detected diseased portion to be treated on the spot by way of the inserted ultrasound endoscope. In order to permit treatments within or from a body cavity, ultrasound endoscopes are usually provided with a biopsy channel or instrument channel coextensively within an endoscopic insertion instrument for insertion therethrough of a treating instrument such as forceps, high frequency treating instrument or the like. A treating instrument of this sort is extended into a patient's body cavity through an exit opening at the distal end of the endoscopic insertion instrument. For accurate manipulation of the treating instrument within a body cavity, it is desirable for the operator to be able to constantly monitor and confirm from outside the position and posture of the treating instrument which is projected into the body cavity through the endoscopic insertion instrument. This is possible with ultrasound endoscopes which are equipped with an ultrasound scan system, in contrast to ordinary endoscopes which do not. For instance, a puncture instrument with a sharp-pointed puncture needle can be monitored from outside and manipulated accurately as it is projected into a body cavity from an endoscopic biopsy channel and penetrated into a target portion for injection of a medicinal liquid or for aspiration of a bleeding site.

For monitoring purposes, a treating instrument which is projected into a body cavity through an opening at the distal end of an endoscopic biopsy channel should be firstly within a view field of an image pickup of an endoscopic observation system, and, after penetration into an intracavitary wall or internal organ, within a view field of an ultrasound scan system. For this purpose, the distal end opening of the endoscopic biopsy channel needs to be located between an image pickup window of an endoscopic observation system and a scanner of an ultrasound examination system.

More particularly, in order to have a puncture instrument invariably within the view fields of both endoscopic observation system and ultrasound examination system, it is conceivable to arrange an ultrasound endoscope in the manner as follows. Firstly, the endoscopic observation system can employ an oblique view type image pickup having a view field in an angular direction relative to the axis of the insertion instrument of the ultrasound endoscope, in combination with an ultrasound scanning system of an electronic scan type which has a large number of ultrasound transducer elements arranged in the axial direction of the endoscopic insertion instrument in order to secure a wide scanning range which substantially overlaps the view field of the endoscopic image pickup. In such a case, the distal end opening of the biopsy channel on the endoscopic insertion instrument is arranged such that a treating instrument can protrude into a body cavity in a direction parallel with or at a shallow angle with the center axis of the view field of the endoscopic image pickup portion.

Regarding the treating instrument, a puncture instrument usually includes a puncture needle member consisting of a rigid pipe of a certain length. On the other hand, the endoscopic insertion instrument has a flexible structure except the distal end section which is constituted by a rigid casing structure. Normally, angle section or a flexible joint is interposed between the rigid distal end section and the flexible main body of the insertion instrument, allowing to turn the direction of the view field of an endoscopic image pickup on the rigid distal end section through a large angle. Therefore, the endoscopic insertion instrument which has been introduced into a body cavity of a patient may have the rigid distal end section in such an angularly bent form as to completely block passage of a rigid needle portion of a puncture instrument. In order to avoid this, it has been the general practice to place a treating instrument like a puncture needle into the endoscopic biopsy channel before insertion into a body cavity of a patient. Since the needle of the puncture instrument is rigid and sharp-pointed, it should always be retained in a retracted position within the endoscopic biopsy channel and kept out of contact with intracavitary walls except when it is driven forward for penetration into an intracavitary wall or into an internal organ which needs a treatment.

To cope with a deep penetration, the puncture instrument needs to have a rigid needle portion of an increased length. On the other hand, from the standpoint of moving the puncture instrument back and forth or in projecting and retracting directions within the biopsy channel of an endoscopic insertion instrument which has a rigid fore distal end section connected to its fore end through an angle section or a flexible joint, it is more convenient to locate the rigid puncture needle substantially in the rigid fore distal end section, and to locate a flexible tube, which is connected to the proximal end of the rigid puncture needle, in the flexible section of the endoscopic insertion instrument rearward of the angle section. Nevertheless, the rigid distal end section of the endoscopic insertion instrument is normally required to have as small an axial length as possible for the purpose of ensuring smooth introduction into a body cavity and at the same time for lessening the pains on the part of the patient. It follows that, in case the puncture needle has an increased length, it might become difficult to accommodate the puncture needle within the length of the inflexible rigid distal end section of the endoscopic insertion instrument. Especially, in the case of an ultrasound endoscope having a bent pipe connected to the fore end portion of a biopsy channel as a shunt passage for projecting a treating instrument obliquely into the view field of an oblique view type endoscopic image pickup, a proximal end portion of the rigid puncture needle is necessarily located partly in the bent portion of the shunt pipe in a forcibly bent form.

Taking the foregoing situations into consideration, the sharp-pointed end of a long puncture needle has to be positioned as closely to the distal end opening of the endoscopic biopsy channel as possible. When the angle section of the endoscopic insertion instrument is flexed to turn the rigid distal end section into the direction of a target, however, the puncture needle could be accidentally projected out of the biopsy channel of the endoscopic insertion instrument, depending upon the turning angle. Further, a proximal end portion of the puncture instrument, which is led out of the endoscopic insertion instrument through an opening at the proximal end of the biopsy channel, is manipulated by an operator to push the puncture instrument in the forward direction for projecting the puncture needle into a penetrating position. The sharp-pointed fore end of the puncture needle in a retracted rest position, however, could be instantly projected out of the biopsy channel when the puncture needle is accidentally pushed forward even in a slight degree. In this regard, according to the prior art, it has been difficult to monitor the position of the sharp-pointed fore end of the puncture needle within the view field of an endoscopic image pickup until the puncture instrument is projected over a certain length from the distal opening of the endoscopic biopsy channel. Namely, it has thus far been difficult to check, within the view field of the endoscopic image pickup, the position of the sharp-pointed end of the puncture instrument in or in the vicinity of the distal opening of the biopsy channel. Therefore, even if the sharp-pointed end of the puncture needle is slightly projected from the distal opening of the biopsy channel for some reason, in many cases this cannot be recognized by the operator.

From the standpoint of safe use or safe treatment, a puncture instrument, when at rest, should be retracted sufficiently to a deep position within the biopsy channel at least while the endoscopic insertion instrument is disposed in a body cavity of a patient. However, because of a short axial length of the rigid distal end section of the endoscopic insertion instrument, it is often found difficult to retract the rigid puncture needle smoothly into and out of the endoscopic biopsy channel unless it is reduced in length to such an extent as would make deep penetrations infeasible.

SUMMARY OF THE INVENTION

In view of the foregoing situations, it is an object of the present invention to provide an ultrasound endoscope which is so arranged as to hold a puncture instrument or a similar treating instrument at an outlet opening of an instrument passage within a view field of an endoscopic observation system, permitting an operator to monitor and check the position of the puncture instrument for safety purposes.

It is another object of the present invention to provide an ultrasound endoscope which can guarantee safe operation of a puncture instrument with a sharp-pointed puncture needle at the time of protrusion out of an instrument passage or similar treating instrument guide means provided on the endoscope.

It is still another object of the present invention to provide an ultrasound endoscope which is so arranged as to ensure smooth protrusion and retraction of a puncture instrument or a similar treating instrument out of and into an outlet opening of an instrument passage provided on the endoscope.

According to the present invention, for achieving the above-stated objectives, there is provided an ultrasound endoscope having a rigid distal end casing of a generally cylindrical shape at a distal end of an elongated flexible insertion instrument and having an ultrasound scanner and an endoscopic image pickup mounted on fore and rear end portions of the distal end casing. The ultrasound endoscope according to the present invention is characterized in that it comprises: an oblique view type endoscopic image pickup fitted in an angularly inclined surface provided on the rear end portion of the distal end casing and having a view field in an obliquely forward direction of the distal end casing; and an instrument outlet opening formed in the distal end casing to project a treating instrument therethrough, the instrument outlet opening being formed in an intermediate position between the ultrasound scanner and the endoscopic image pickup and within a view field of the endoscopic image pickup.

In this instance, the instrument outlet opening is preferably formed in a substantially flat surface portion which is provided in the axial direction on the distal end casing and at the outer end of an instrument passage which is angularly inclined in the same direction as the view field of the endoscopic image pickup. By so arranging, a treating instrument at the instrument outlet opening, which is in the view field of the endoscopic image pickup, can be monitored by way of an endoscopic observation system to check its position for safety purposes, from a slightly projected position to a largely projected position whenever it gets out of the instrument outlet opening. The ultrasound scanner can be constituted by a multi-element electronic scan type transducer which has a large number of transducer elements arranged in the axial direction of the endoscopic insertion instrument. Preferably, the transducer elements are arranged in a convex shape with an apex portion protruding to a point in level with or beyond the above-mentioned instrument outlet opening

BRIEF DESCRIPTION OF THE DRAWINGS

The above and other objects, features and advantages of the present invention will become apparent from the following description, taken in conjunction with the accompanying drawings which show by way of example a preferred embodiment of the invention, and in which.

DESCRIPTION OF PREFERRED EMBODIMENTS

Figure 1:
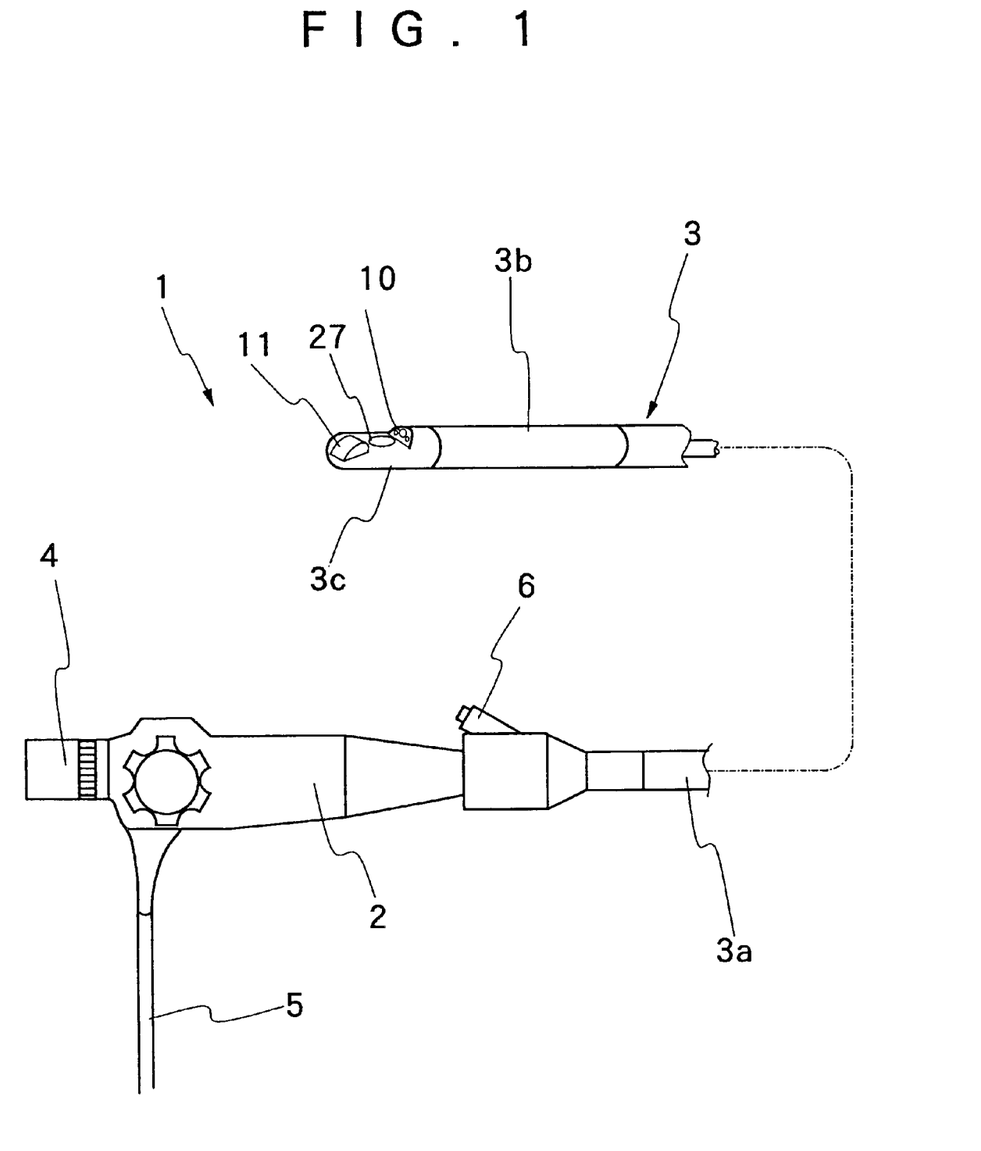
FIG. 1 is a schematic illustration showing general layout of an ultrasound endoscope embodying the present invention.

Hereafter, the present invention is described more particularly by way of its preferred embodiment with reference to the accompanying drawings. Firstly, referring to FIG. 1 which shows the general layout of an ultrasound endoscope, indicated at 1 is the ultrasound endoscope, including a head grip assembly 2 to be gripped and manipulated by an operator, and an elongated insertion instrument 3 extended forward from the head grip assembly 2 for introduction into a body cavity of a patient. The endoscopic insertion instrument 3 includes, from its proximal end which is connected to the head grip assembly 2, a flexible section 3a which constitutes a major part of the elongated insertion instrument 3 and which is flexibly bendable in arbitrary directions to comply with bends in a path of insertion, if any, an angle section or flexible joint 3b which is connected to the fore end of the flexible section 3a, and a rigid distal end section 3c constituted by a rigid distal end casing structure of a generally cylindrical shape which is connected to the fore end of the angle section 3b. An eyepiece 4 is provided on the rear side of the head grip assembly 2, i.e., on the side away from the insertion instrument 3. Further, a universal cable 5 which is led out from the head grip assembly 5 of the ultrasound endoscope 1 is disconnectibly connected to a light source and an ultrasound image observation terminal which are not shown in the drawings.

Figure 2:
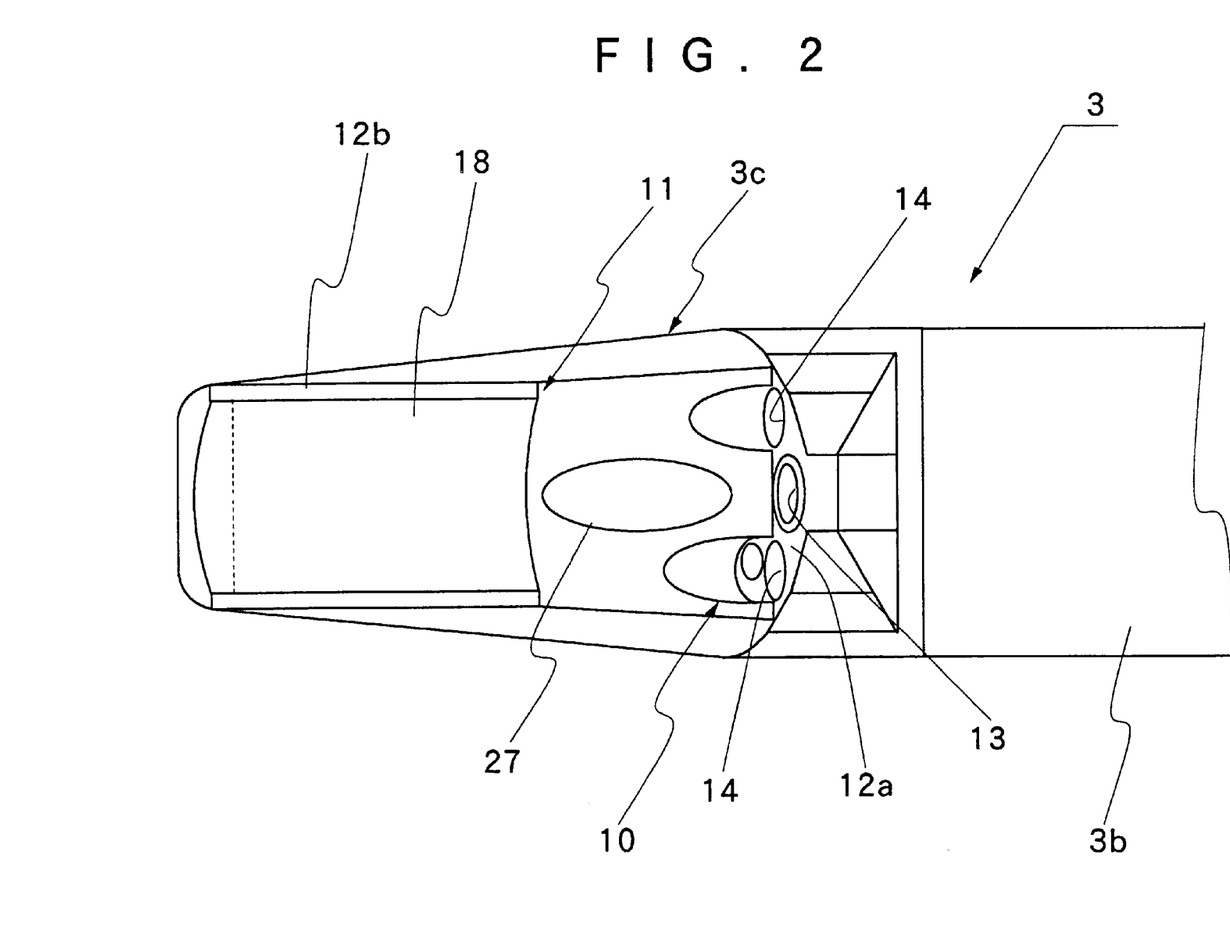
FIG. 2 is a schematic plan view of a distal end portion of an elongated endoscopic insertion instrument.
Figure 3:
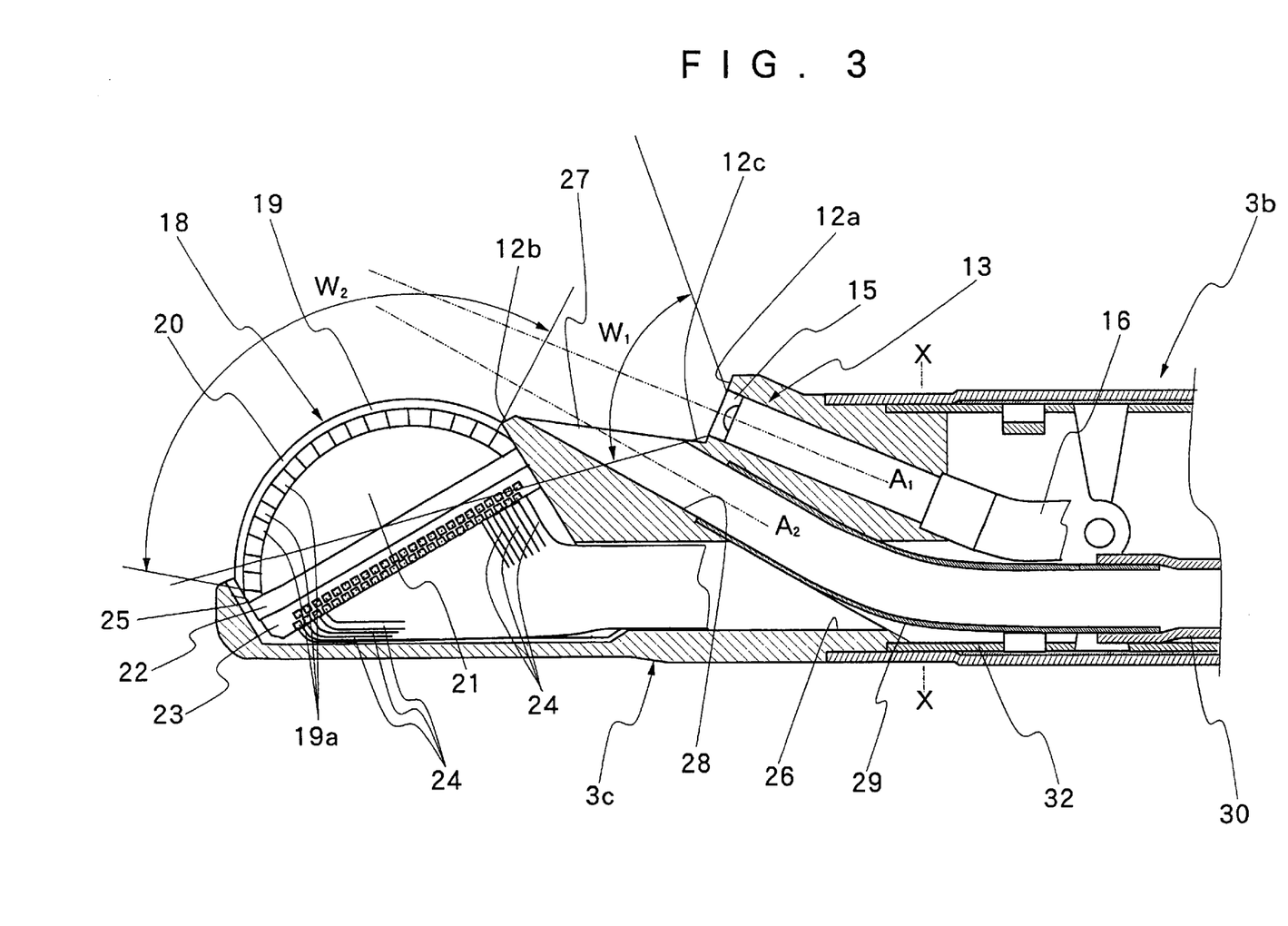
FIG. 3 is a longitudinal sectional view of the distal end section of the endoscopic insertion instrument.

Referring to FIGS. 2 and 3 which show the endoscopic insertion instrument 3 in plan and sectional views, the reference numerals 10 and 11 generally indicate an endoscopic image pickup portion and an ultrasound scanner, respectively. The endoscopic image pickup portion 10 includes an observation window 13 which is located on and fitted in a first inclined surface 12a provided in a rear end portion of the distal end casing 3c, and an illumination light emitting portions 14 which are provided on the opposite sides of the image pickup portion 13. As seen particularly in FIG. 3, the image pickup portion 13 is of an oblique view type which has the center line $A_1$ of its view field inclined through a predetermined angle relative to the center axis $A_2$ of the endoscopic insertion instrument 3. Further, the endoscopic image pickup portion 13 has an observation view field $W_1$ of wide angle.

The image pickup portion 13 includes an objective lens 15, and an image guide 16 in the form of a bundle of fiber optics having an input end located at the focus of the objective lens 15. The image guide 16 is extended to the eye piece 4 through the endoscopic insertion instrument 3 and the head grip assembly 2. The image guide 16, however, may be replaced by a solid-state image sensor in case there is an extra space within the endoscopic insertion instrument 3 at a position in the vicinity of the objective lens 15. Further, the illumination light emitting portions 14 are each provided with an illuminating lens on the front side of an output end of an illumination light guide 17 (FIG. 4) which is also constituted by a bundle of fiber optics. The illumination light guide 17 is passed through the universal cable 5 for connection to a light source. Upon connecting the universal cable 5 to the light source, illuminating light is transmitted through the light guide 17 and projected through the light emitting portions 14 to illuminate an intracavitary portion under observation.

On the other hand, the ultrasound scanner 11 of the ultrasound examination system is located on and fitted in a second inclined surface 12b which is provided in a fore end portion of the distal end casing 3c of the endoscopic insertion instrument 3 forward of the endoscopic image pickup window 10, and provided with an ultrasound transducer 18 in the form of a multi-element electronic scan type transducer 19 having a large number of transducer elements 19a arranged in a row and in an arcuately convex shape as a whole in the axial direction of the endoscopic insertion instrument 3. Thus, the ultrasound scanner 11 is positioned forward of the endoscopic image pickup window 10. An acoustic lens 20 is fitted on the front side of the transducer unit 19, which is supported by a backing material 21 on the rear side thereof. Further, provided on the rear side of the backing material 21 is a substrate 22 for a flexible wiring member 23 which serves to make connections with a predetermined number of wires 24 from the universal cable. Each transducer element 19a of the transducer unit 19 is driven to transmit an ultrasound signal by applying a voltage across the electrodes which are provided on the front and rear sides of the transducer element. More specifically, the transducer unit 19 is provided with one common electrode on one side and a large number of electrodes on the other side correspondingly to the respective transducer elements 19a, and the wires 24 are respectively connected to these electrodes.

In the case of the ultrasound transducer unit 19 having a large number of transducer elements 19a arranged in a convex form as described above, for example, an electronic convex scan is made upon sequentially driving the transducer elements 19a to produce a tomographic ultrasound image of a sector form giving information on body tissues in the scanned sectoral area. Indicated at $W_2$ in FIG. 3 is the view angle of the ultrasound image, that is to say, the scan range of the ultrasound scanner 11, which largely overlaps the view field $W_1$ of the image pickup portion 13 of the endoscopic observation system 11.

Figure 4:
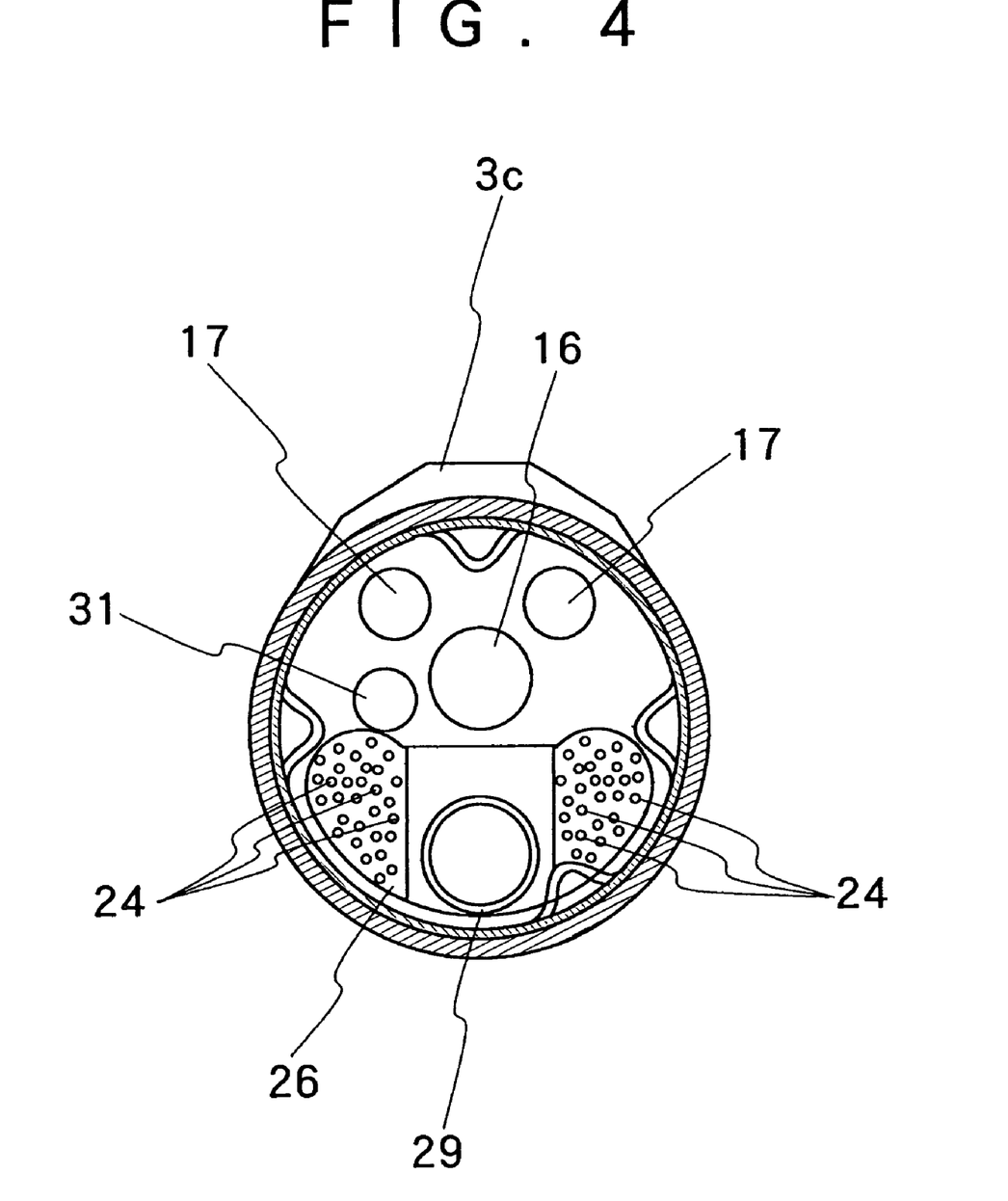
FIG. 4 is a cross-sectional view taken on line X—X of FIG. 3.

In this instance, the ultrasound transducer 18 of the ultrasound scanner 11, which is in the foremost position on the distal casing structure 3c, is located on the second inclined surface 12b of a smaller inclination angle than the first inclined surface 12a. The ultrasound transducer 18 is fixedly fitted in an opening 25 which is formed in the second inclined surface 12b of the distal casing structure 3c. Further, as shown in FIG. 4, the wires 24 which are connected to the wiring member 23 are extended to and beyond the angle section 3b by way of a wiring space 26 which is provided axially through the endoscopic insertion instrument 3.

Opened on the distal end casing 3c between the endoscopic image pickup portion 10 and the ultrasound scanner 11 is a treating instrument outlet or exit opening 27 through which a treating instrument is to be projected. This instrument outlet 27 is opened in a flat surface 12c intervening between the first and second inclined surfaces 12a and 12b and at a distal end of an instrument passage 28 which is formed in the distal end casing 3c. A rigid instrument passage pipe 29 which is fitted in the instrument passage 28 is connected to an endoscopic biopsy channel 30 which is constituted by a flexible tube. In this instance, the instrument passage 28 is arranged in such a way as to project a treating instrument in a direction parallel with or almost parallel with a center line of a view field of the image pickup portion 13 of the endoscopic observation system 10. In contrast, the biopsy channel 30 is extended in the axial direction of the endoscopic insertion instrument 3. The instrument passage pipe 29 functions as a link member which connects the biopsy channel 30 with the instrument passage 28, and at the same time as a pointing member which directs a treating instrument in movement in the axial direction of the endoscopic insertion instrument 3 angularly toward the instrument passage 28 in the distal end casing 3c. Accordingly, on the proximal side of the angularly diverging instrument passage 28, the instrument passage pipe 29 is curved to extend ultimately in the axial direction of the endoscopic insertion instrument at its proximal end which is connected to the biopsy channel 30. In the drawing, indicated at 31 is a liquid passage which is provided in and axially through the endoscopic insertion instrument for pumping a liquid like water into a body cavity.

Figure 5:
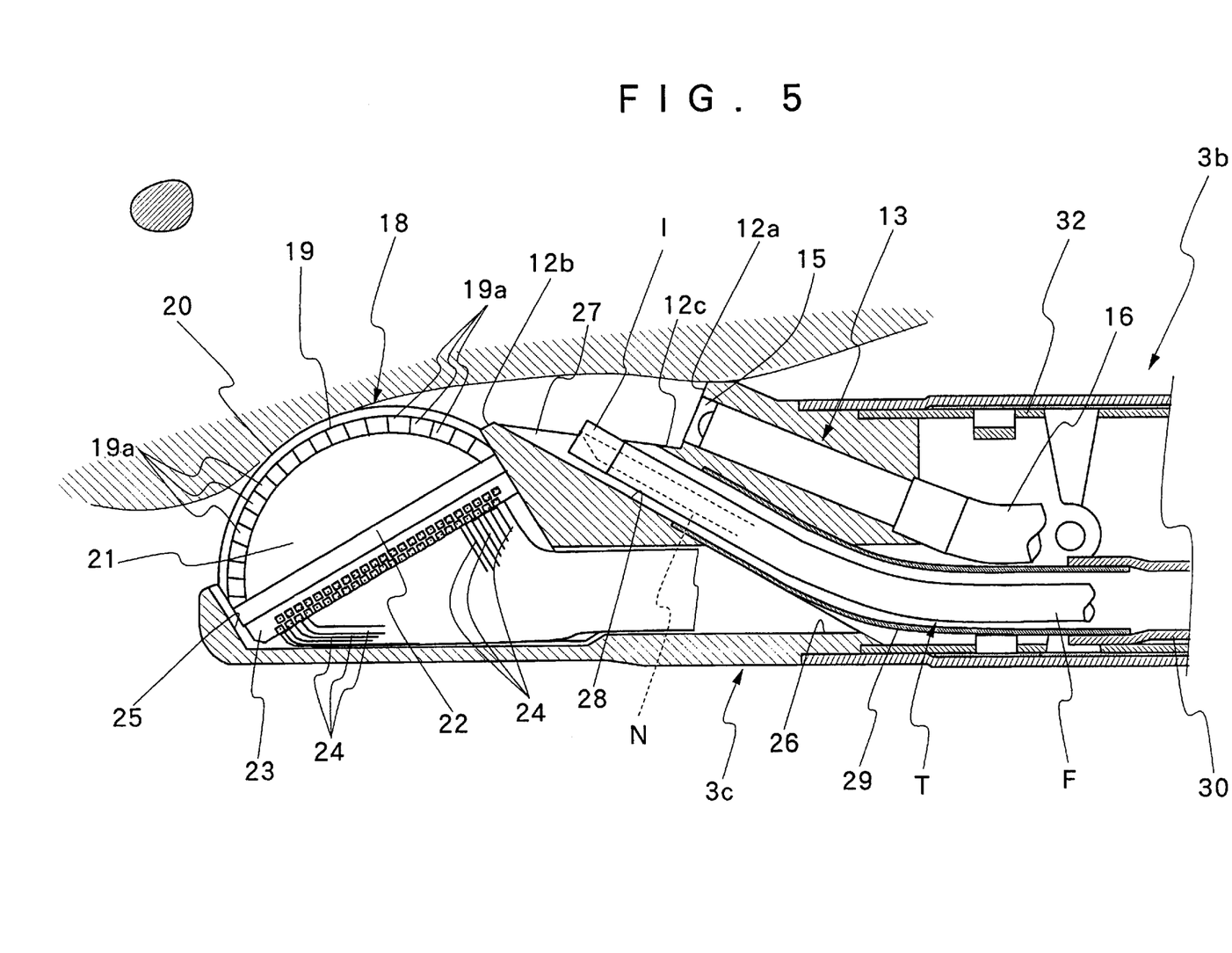
FIG. 5 is a longitudinal sectional view of the fore distal end section of the endoscopic insertion instrument, with a puncture instrument retracted into an instrument passage shunted from a biopsy channel of the endoscope.
Figure 6:
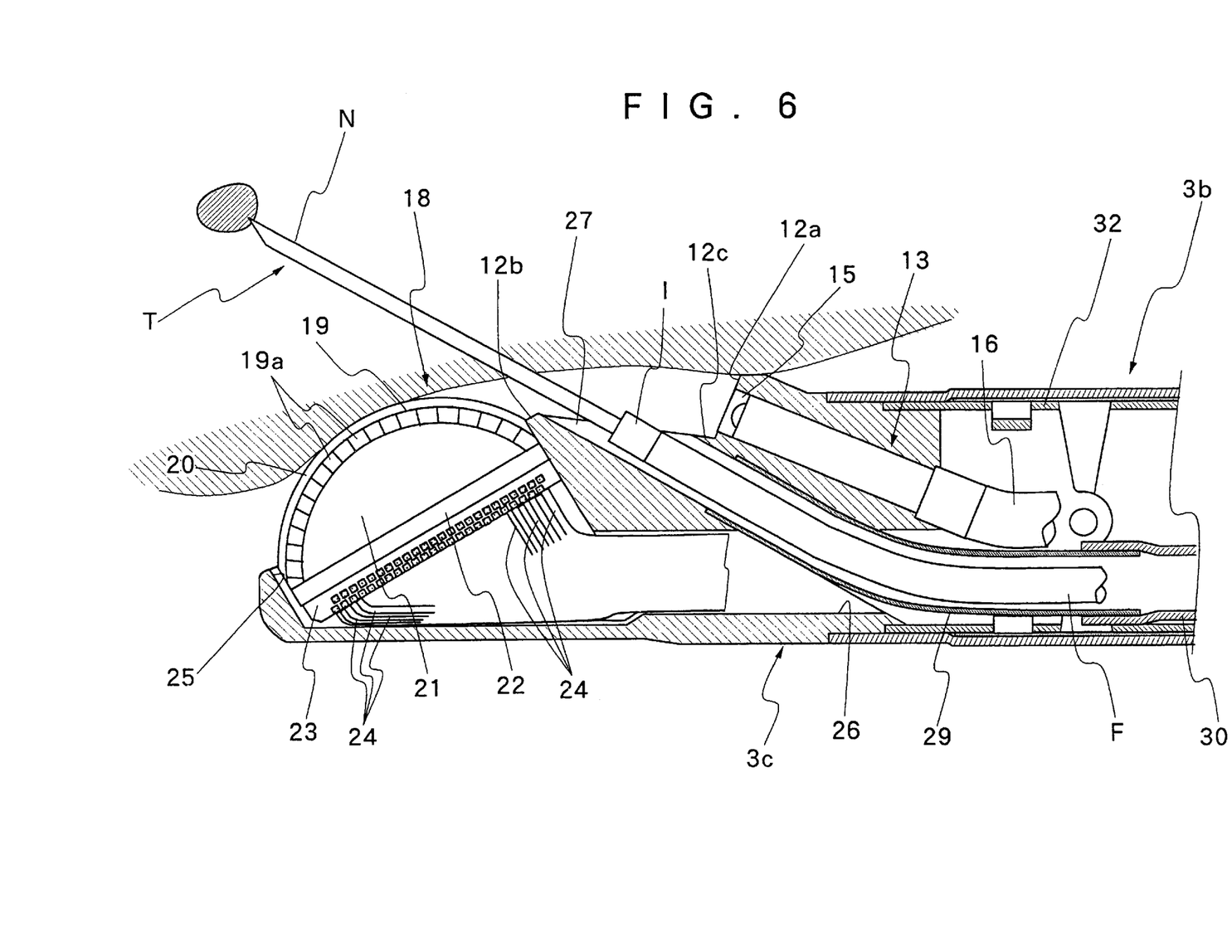
FIG. 6 is a view similar to FIG. 5 but showing the puncture instrument in a projected position.

With the construction as described above, in addition to the endoscopic observation system 10 and the ultrasound scanner 11, the ultrasound endoscope 1 is provided with the instrument passage which extends from the biopsy channel 30 to the instrument outlet opening 27 through the link pipe 29 and the instrument passage 28, permitting to introduce a suitable treating instrument into a body cavity for treatment of a diseased portion whenever necessary. The treating instruments which can be inserted through the instrument passage includes not only those instruments which are flexible as a whole like forceps and high frequency, but also rigid instruments like a puncture instrument as shown in FIGS. 5 and 6.

The puncture instrument T is composed of a flexible sleeve F, a sharp-pointed puncture needle N in the form of a rigid narrow pipe of a predetermined length which is loosely fitted in the flexible sleeve F, and a flexible narrow tube which is (not shown) which is connected to the proximal end of the puncture needle N. Connected to the fore distal end of the flexible sleeve F is a rigid ring which provides an annular instrument outlet I with an inside diameter slightly larger than the outside diameter of the puncture needle N. Accordingly, the puncture needle N can be projected in a predetermined direction under the guidance of the instrument outlet I.

Since the puncture needle N consists of a rigid pipe, it is difficult to pass the needle through an acutely bent portion. Therefore, the puncture instrument T is placed into the ultrasound endoscope 1 as shown in FIG. 5 in a preparatory stage or before introducing the endoscopic insertion instrument 3 into a body cavity of a patient. At this time, the sharp-pointed end of the puncture needle N is held in a retracted position within the instrument outlet I at the distal end of the flexible sleeve F, and the puncture needle N itself is located within the instrument passage pipe 29 forward of the endoscopic biopsy channel 30. The angle section 3b of the endoscopic insertion instrument 3 is constituted by a number of successively connected angle rings, of which the foremost angle ring 32 is directly connected to the distal end casing 3c. Namely, the endoscopic insertion instrument 3 has a rigid portion which extends from its distal end to the proximal end of the foremost angle ring 32. Therefore, the instrument passage pipe 29 is extended as far as or to a point in the vicinity of the proximal end of the foremost angle ring 32 which constitutes part of the rigid distal end section of the endoscopic insertion instrument 3. When so arranged, the proximal end of a relatively long puncture needle N can be located within the instrument passage pipe 29.

The instrument passage pipe 29 plays the role of a shunt for diverting a treating instrument from the axially extending biopsy channel 30 toward the angular instrument passage 28. However, a bend in the instrument passage pipe 29 should be as moderate as possible in order to accommodate the puncture needle N therein without causing the latter to bend to any conspicuous degree. For this purpose, as shown in the drawings, the instrument passage pipe 29 is gradually bent from a pipe portion behind the instrument passage 28 and extended substantially into contact with the inner periphery of the foremost angle ring 32 before it is connected with the endoscopic biopsy channel 30. Thus, the instrument passage pipe 29 is bent through an extremely moderate curve which can ensure smooth projection and retraction of the puncture needle N from and into the treating instrument passage pipe 29.

As the treating instrument passage pipe 29 is turned and extended in the above-described manner, substantially in contact with the foremost angle ring 32, it occupies part of the axial wiring space 26 in the endoscopic insertion instrument 3. A large number of wires 24 to or from the ultrasound transducer 18 are accommodated in and extended through the axial wiring space 26. Since the wires 24 are in an unbundled state, they can be passed through the axial wiring space 26 irrespective of the shape of the latter as long as the wiring space 26 is broader than the total sectional area of the wires. Accordingly, the axial wiring space 26 can be used effectively by accommodating the instrument passage pipe 29 along with the wires 24.

As explained hereinbefore, the endoscopic image pickup portion 13 is formed in the first inclined surface 12a while the instrument outlet opening 27 is formed in the flat portion 12c of the distal end casing 3c of the endoscopic insertion instrument 3. The endoscopic image pickup portion 13 is located closely to the flat portion 12c, and the instrument outlet opening 27 is located closely to the first inclined surface 12a. Therefore, as seen particularly in FIG. 3, the instrument outlet opening 27 is positioned within the view field of the endoscopic image pickup portion 13. Namely, the instrument outlet opening 27 as a whole and part of the instrument passage 28 can always be viewed or monitored by way of the endoscopic observation system. Besides, the ultrasound transducer 18 is arranged in a convex shape, and its apex portion is projected above or substantially at the same height as the flat portion 12c of the distal end casing 3c. Therefore, the instrument outlet opening 27 is opened at a recessed or sunken position in the profile of the distal end casing 3c as a whole.

In case the ultrasound endoscope 1 is arranged as described above, after introducing the endoscopic insertion instrument 3 into a body cavity of a patient to locate the distal end casing 3c at a site of examination, an intracavitary portion of interest can be examined firstly by the use of the endoscopic observation system, and, if a diseased portion is spotted by the endoscopic examination, information internal body tissues in the diseased portion can be acquired by ultrasound scans. In addition, it is possible to give a suitable treatment to the diseased portion if necessary. For example, the puncture needle N of the treating instrument T is penetrated into the diseased portion to inject a medicine or to suck out body fluids.

At the time of introducing the endoscopic insertion instrument 3 into a body cavity along a path of insertion, the angle section 3b is flexed by the operator in the directions of turns which may exist in the path of insertion, while the flexible section 3a can adapt itself to bends in the path of insertion by itself. The puncture instrument T is provided with the puncture needle N of a necessary length for penetration into a predetermined depth within a patient's body. Therefore, it may become difficult to place the puncture instrument T in the endoscopic insertion instrument 3 after introduction into a body cavity of a patient if the flexible section 3a and/or the angle section 3b is in a bent form. To avoid this, the puncture instrument T with a rigid needle member is preferred to be placed in the endoscopic biopsy channel 30 of the endoscopic insertion instrument 3 prior to introduction into a body cavity.

At the time of placement in the endoscopic insertion instrument 3, the puncture needle N and the tube member which is connected to the needle N are fitted in the flexible sleeve F, with the sharp-pointed fore end of the puncture needle N retained in a retracted position inward of the instrument outlet I which is constituted by a rigid pipe. Then, the flexible sleeve F of the puncture instrument T is put into the endoscopic biopsy channel 30 through an entrance way 6 which is provided on a casing of the head grip assembly 2 of the endoscope 1, and pushed toward the instrument outlet opening 27 through the instrument passage pipe 29 and the instrument passage 28. Outside a patient's body, the endoscopic insertion instrument 3 can be retained in a straight form, so that the puncture instrument T can be easily and smoothly put into the straightened endoscopic biopsy channel 30.

Shown schematically in FIG. 5 is the ultrasound endoscope 1 in use for an ultrasound scan. At the time of an ultrasound scan, the ultrasound transducer 18 is held in intimate contact with an intracavitary wall. The position of the ultrasound scanner can be checked or monitored by way of the endoscopic image pickup portion 13 of the endoscopic observation system 10. At the time of monitoring the scanner position through the endoscopic image pickup portion 13, the distal end casing 3 of the endoscopic insertion instrument 3 is held in a position which is spaced to some extent from the intracavitary wall. While monitoring the scanner position in this way, the ultrasound transducer 18 is shifted to the proximity of or into abutting engagement with an intracavitary portion to be scanned. At this time, the puncture needle N could come into contact with an intracavitary wall if the puncture instrument T is projected out of the instrument outlet opening 27, more specifically, if the pointed end of the puncture needle N is projected through the outlet ring I even in a slight degree.

Since the major part of the endoscopic insertion instrument 3 is flexible and bendable by itself along a path of insertion, its bending movements could cause the puncture instrument T as a whole to move back and forth within the instrument passage 28 and as a result the puncture needle N could protrude out of the instrument outlet opening 27, due to a difference between the outside and inside diameters of the flexible sleeve F and the endoscopic biopsy channel 30 and also due to a difference in diameter of the flexible sleeve F from the puncture needle N and the flexible tube. Therefore, for safety purposes, the puncture needle N should be retained in a more deeply retracted position within the instrument passage 28. However, deep retraction of the puncture instrument T is difficult unless the length of the rigid puncture needle N is reduced to limit the depth of its penetration.

In this regard, according to the present invention, the endoscope is arranged such that the instrument outlet opening 27 and part of the instrument passage 28 fall within the view field of the image pickup portion 13 of the endoscopic observation system 10, permitting the operator to constantly check or monitor the position or status of the puncture instrument T, particularly, of the puncture needle N by way of endoscopic observation images. Accordingly, when the puncture instrument T, especially, the puncture needle N spontaneously comes into a protruding position in the course of insertion into a body cavity, it can be pulled into a retracted safe position by the operator. Besides, when the ultrasound transducer 18 is brought into intimate contact with an intracavitary wall for an ultrasound examination as shown in FIG. 5, the puncture instrument T as a whole can be retained in a safe position spaced away from the intracavitary wall under examination.

As soon as a diseased portion is spotted as a result of an ultrasound scan, the puncture instrument T, with the puncture needle N in a retracted position inward of the instrument outlet ring I, is advanced until it comes into intimate contact with the intracavitary wall. Then, in this state, the puncture needle N is driven forward to penetrate into the intracavitary wall. At this time, as shown in FIG. 6, despite a relatively large resistance force, a sufficient thrust force for penetration into the diseased portion can be applied to the puncture needle N which is made of a rigid pipe or tube. Besides, the puncture needle N of the puncture instrument T can be of a length which is sufficient for penetration into a diseased portion at a deep position.

At the time of a penetrating treatment as described above, the position of the puncture instrument T can be constantly monitored through the endoscopic observation system 10 and therefore can be precisely adjusted, from a time point when it is initially projected through the instrument outlet opening 27 and until it is intimately contacted with an intracavitary wall under examination, for ensuring a higher target hitting rate. After the puncture needle N is penetrated into a patient's body, it is difficult to monitor its penetrated fore end portion by way of images of the endoscopic observation system 10. However, instead, the penetrated needle portions can be monitored by way of ultrasound images upon activating the transducer 18 of the ultrasound scan system 11. Accordingly, with reference to an ultrasound image of the puncture needle N within a tomographic ultrasound observation range, the puncture needle N can be smoothly and precisely directed toward a diseased portion in a very safe manner without causing destruction of healthy cells. Upon the puncture needle N reaching a target diseased portion, a suitable treatment can be given thereto through the needle, for example, injection of a medicinal liquid, aspiration from a bleeding site etc.

In the particular embodiment shown, the endoscope is arranged such that the instrument outlet opening 27 as a whole comes into the view field of the image pickup portion 13 of the endoscopic observation system 10. However, the entire instrument outlet opening 27 may not necessarily be within the view field of the endoscopic observation system 10. Particularly, the top end of the first inclined surface 12a is at a higher level than the flat surface portion 12c with the instrument outlet opening 27, and part of the transducer 18 is also located at a higher level than the flat portion 12c. Namely, the flat portion 12c is indented in the profile of the distal end casing 3c. Therefore, when the distal end casing 3c is brought into intimate contact with an intracavitary wall under examination, the flat portion 12c is located at a certain distance from the intracavitary wall and kept out of contact with the latter even if the puncture needle N is slightly projected from the instrument outlet opening 27. Accordingly, it suffices if at least part of the instrument outlet opening 27 is in the view field of the endoscopic image pickup portion 13, for taking note of spontaneous protrusion of the puncture instrument T before contacting an intracavitary wall or for confirming projecting direction of the puncture instrument T. Needless to say, treating instruments other than the above-described puncture instrument T can be similarly monitored by way of the endoscopic observation system.

What is claimed is:

1. An ultrasound endoscope having a rigid distal end casing of a generally cylindrical shape at a distal end of an elongated flexible insertion instrument and having an ultrasound scanner and an endoscopic image pickup mounted on fore and rear end portions of said distal end casing, said ultrasound endoscope comprising:

an oblique view type endoscopic image pickup fitted in an angularly inclined surface provided on said rear end portion of said distal end casing and having a view field in an obliquely forward direction of said distal end casing; and an instrument outlet opening formed in said distal end casing to project a treating instrument therethrough, said instrument outlet opening being formed in an intermediate position between said ultrasound scanner and said endoscopic image pickup and within a view field of said endoscopic image pickup.

2. An ultrasound endoscope as defined in claim 1, wherein said instrument outlet opening is formed in a substantially flat surface provided axially between said fore and rear end portions of said distal end casing, and inclined through a predetermined angle toward the direction of said view field of said endoscopic image pickup.

3. An ultrasound endoscope as defined in claim 2, wherein said transducer of said ultrasound scanner is of a multi-element electronic scan type having a large number of transducer elements arranged in the axial direction of said endoscopic insertion instrument in a convex shape with an apex portion protruding to a point in level with or beyond said flat surface containing said instrument outlet opening.

4. An ultrasound endoscope as defined in claim 3, wherein said transducer is fitted in a second inclined surface provided in said fore end portion of said distal end casing.

* * * * *